United States Patent
Walsh

(10) Patent No.: US 7,986,143 B2
(45) Date of Patent: Jul. 26, 2011

(54) MULTICOIL LOW-FIELD NUCLEAR MAGNETIC RESONANCE DETECTION AND IMAGING APPARATUS AND METHOD

(75) Inventor: David O. Walsh, Mukilteo, WA (US)

(73) Assignee: Vista Clara Inc., Mukilteo, WA (US)

( * ) Notice: Subject to any disclaimer, the term of this patent is extended or adjusted under 35 U.S.C. 154(b) by 0 days.

(21) Appl. No.: 12/672,503

(22) PCT Filed: Nov. 10, 2008

(86) PCT No.: PCT/US2008/082969
§ 371 (c)(1),
(2), (4) Date: Feb. 5, 2010

(87) PCT Pub. No.: WO2005/017549
PCT Pub. Date: Feb. 24, 2005

(65) Prior Publication Data
US 2011/0095758 A1 Apr. 28, 2011

Related U.S. Application Data

(60) Provisional application No. 60/986,904, filed on Nov. 9, 2007.

(51) Int. Cl.
*G01V 3/00* (2006.01)
(52) U.S. Cl. ......................... 324/318; 324/309
(58) Field of Classification Search .......... 324/300–322; 600/407–445; 335/300, 299, 216; 505/90, 505/220, 231; 333/219, 235
See application file for complete search history.

(56) References Cited

U.S. PATENT DOCUMENTS

| | | |
|---|---|---|
| 3,019,383 A | 1/1962 | Varian |
| 4,727,324 A | 2/1988 | Bendall et al. |
| 4,812,760 A | 3/1989 | Bottomley et al. |
| 4,975,644 A | 12/1990 | Fox |
| 5,144,243 A | 9/1992 | Nakabayashi |

(Continued)

FOREIGN PATENT DOCUMENTS

EP 017058 2/1986

(Continued)

OTHER PUBLICATIONS

Walsh, filing receipt for U.S. Appl. No. 12/715,115, filed Mar. 1, 2010.

(Continued)

*Primary Examiner* — Brij B Shrivastav
(74) *Attorney, Agent, or Firm* — Jensen & Puntigam, P.S.; Nathaniel Ari Gilder

(57) ABSTRACT

A multicoil NMR detection and imaging apparatus allows multicoil NMR detection and imaging to be performed efficiently at low operating frequencies. The apparatus comprises an AC voltage generator, a transmit switching circuit, a coil switching network, an array of two or more detection coils, a set of receive switching circuits with one switching circuit for each detection coil, and a set of preamplifier circuits with input impedance substantially greater than the impedance of each respective detection coil at the intended operating frequency. The AC generator produces an alternating current waveform that is routed through one of more detection coils during transmit mode while the preamplifier circuits are isolated from the detection coil(s). During receive mode the AC generator is isolated from the detection coils to prevent noise from the transmitter from degrading the quality of received signals.

30 Claims, 11 Drawing Sheets

U.S. PATENT DOCUMENTS

| | | | |
|---|---|---|---|
| 5,545,995 | A | 8/1996 | Schneider et al. |
| 5,759,152 | A | 6/1998 | Felmlee et al. |
| 6,107,797 | A | 8/2000 | Sezginer |
| 6,160,398 | A | 12/2000 | Walsh |
| 6,201,395 | B1 | 3/2001 | Stanley |
| 6,366,086 | B1 | 4/2002 | Sen |
| 6,459,265 | B1 * | 10/2002 | Lou et al. ............. 324/322 |
| 6,477,398 | B1 | 11/2002 | Mills |
| 6,593,740 | B1 | 7/2003 | Van Den Brink et al. |
| 6,845,262 | B2 | 1/2005 | Albert |
| 6,969,992 | B2 | 11/2005 | Vaughan |
| 7,035,682 | B2 | 4/2006 | Van Den Brink et al. |
| 7,176,689 | B2 | 2/2007 | Machida |
| 7,221,160 | B2 | 5/2007 | Leussler |
| 7,414,402 | B2 | 8/2008 | Habara |
| 7,466,128 | B2 | 12/2008 | Walsh |
| 7,511,496 | B2 * | 3/2009 | Schiano ............... 324/312 |
| 7,791,339 | B2 * | 9/2010 | Wong et al. ............ 324/307 |
| 2003/0122545 | A1 | 7/2003 | Van Den Brink et al. |
| 2006/0186882 | A1 | 8/2006 | Walsh |
| 2009/0224763 | A1 * | 9/2009 | Duensing .............. 324/318 |

FOREIGN PATENT DOCUMENTS

| | | |
|---|---|---|
| EP | 0170508 | 9/1990 |
| EP | 04777777 | 5/2006 |
| GB | 2339024 | 12/2000 |
| WO | WO2004/061469 | 7/2004 |
| WO | 2005017549 | 2/2005 |
| WO | WO2005/017549 | 2/2005 |
| WO | WO2007/030832 | 3/2007 |

OTHER PUBLICATIONS

Hayes, Volume Imaging with MR Phased Arrays, 6 pages, 1999, pp. 10-15.

Legchenko, A Revised Mathematical Model of Magnetic Resonance Sounding, 4 pages, 1999, pp. 12-15.

Legchenko, Industrial Noise and Processing of the Magnetic Resonance Signal, 4 pages, 2005, pp. 7-10.

Hertrich, Surface-NMR with Separated Loops—Investigations on Spatial Resolution, 4 pages, 2000, pp. 8-11.

Warsa, 3-D Modelling and Assessment of 2-D inversion of Surface NMR, 4 pages, 2003, pp. 11-14.

Katscher, transmit SENSE, 7 pages, 2007, pp. 11-17.

Walsh, Adaptive Reconstruction of Phased Array MR Imagery, 9 pages, 2009, pp. 30-38.

Giovannetti, Note: Magnetostatic Simulation for Accurate Design of Low-Field MRI Phased Array Coils, 7 pages, 2008, pp. 8-14.

Krjukov, "Design and Evaluation of a Low Field System for Hyperpolarized 3-He Gas Imaging of Neonatal Lungs" 4 pages, 2000, pp. 10-13.

Leussler, "Intrinsic Hybrid Surface Coil Array for Improved SNR in Cardiac MRI", 2 pages, 2003, pp. 6-7.

De Zanche, "Principles of Array System Design", 8 pages, 2005, pp. 20-24.

Zwart, "Design of a SENSE-Optimized High-Sensitivity MRI Receive Coil for Brain Imaging", 10 pages, 2007, pp. 21-30.

Lersch, Communication in EU Application No. 08848565.1, Including Supplementary EU Search Report, Dated Dec. 30, 2010, 19 pages.

Ryu, Si Ung, International Search Report for PCT/US08/082969, Apr. 10, 2009, 3 pages.

Hayes et al.: "Volume Imaging with MR Phased Arrays"; Magn. Res. Med. 18, 309-319 (1991).

Katscher et al.: "Transmit SENSE"; Mag. Res. Med. 49, 144-156 (2003).

Legchenko, "A Revised Mathematical Model of Magnetic Resonance Sounding", presented at the MRS_2nd International Workshop, Nov. 19-21, 2003 in Orleans, France.

Hertrich, "Surface-NMR with Separated Loops—Investigations on Spatial Resolution", presented at the MRS_2nd International Workshop, Nov. 19-21, 2003 in Orleans France.

Warsa et al., "3-D Modelling and Assessment of 2-D inversion of Surface NMR", presented at the MRS—2nd International Workshop, Nov. 19-21, 2003 in Orleans, France.

Legchenko, "Industrial Noise and Processing of the Magnetic Resonance Signal", presented at the MRS_2nd International Workshop, Nov. 19-21, 2003 in Orleans, France.

Walsh, "Adaptive Reconstruction of Phased Array MR Imagery", Magn. Res. Med. 43, 582-590 (2000).

* cited by examiner

MULTICOIL LOW-FIELD NUCLEAR MAGNETIC RESONANCE DETECTION AND IMAGING APPARATUS AND METHOD

CROSS-REFERENCE TO RELATED APPLICATIONS

This application claims priority of PCT/US2008/082969, filed on Nov. 10, 2008, entitled "MULTICOIL LOW-FIELD NUCLEAR MAGNETIC RESONANCE DETECTION AND IMAGING APPARATUS AND METHOD," and U.S. Provisional Patent Application No. 60/986,904, filed on Nov. 9, 2007, entitled "MULTICOIL NMR DETECTION AND IMAGING APPARATUS," the disclosure of which is incorporated herein by reference in their entirety.

FIELD

The present disclosure relates generally to Nuclear Magnetic Resonance (NMR) imaging and, more specifically, to a multicoil NMR detection and imaging method and apparatus for allowing multicoil NMR detection and imaging to be performed efficiently at relatively low operating frequencies.

BACKGROUND

As is well known, NMR systems have been in use for many years and can be used to provide imaging and/or analysis of a sample being tested. Various different types of NMR are known, including "high-field" NMR that uses relatively high frequency magnetic fields and high static magnetic field strengths, and "low-field" NMR that uses relatively low frequency magnetic fields and low static magnetic field strengths. Typically, low-field NMR systems are comprised of products and devices designed for applications utilizing a single detection channel, and high-field NMR systems are comprised of products and devices designed for applications utilizing single or multiple detection channels. Examples of existing low-field NMR detection products and devices include a single channel Earth's field groundwater detection device, such as described in U.S. Pat. No. 3,019,383, and a single channel commercial groundwater detection products "Numis" and "Hydroscope" which are derived from the design such as described in U.S. Pat. No. 3,019,383. Various multi-channel NMR detection devices have been designed for high-field NMR applications.

A number of specific hardware designs have been developed to simultaneously optimize the NMR signal to noise ratio and minimize mutual coupling between adjacent coils in a multiple coil NMR receive array. In particular, in the field of medical magnetic resonance imaging (MM), the following general approaches to this problem have been developed, some in combination with one another: a) the use of transmission line segments of length equal to an integer multiple of a quarter wavelength at the RF operating frequency, in conjunction with series crossed diodes between the transmitter and the transmit coil(s), to isolate noise from the transmitter during the receive operation, such as described in U.S. Pat. No. 4,739,271; b) the use of a pre-damp circuit, which includes a low input impedance pre-amplifier transformed through a quarter-wavelength transmission line segment to achieve a high input impedance to the coil, thereby reducing currents on the coil during receive mode, and hence reducing coupling between adjacent coils during receive mode, such as described in U.S. Pat. No. 4,885,541; c) the use of ultra-low input impedance preamplifiers to minimize mutual coupling between adjacent coils, such as described in U.S. Pat. No. 6,498,489; and d) the use of capacitive elements between adjacent coils to minimize mutual coupling between adjacent coils.

SUMMARY

The present disclosure provides a new multicoil NMR detection and imaging apparatus construction wherein the same can be utilized for allowing multicoil NMR detection and imaging to be performed efficiently at low operating frequencies. Various embodiments of the present invention, which will be described subsequently in greater detail, provide a new multicoil NMR detection and imaging apparatus that has many of the advantages of the NMR apparatus mentioned heretofore and many novel features that result in a new multicoil NMR apparatus having many advantages over previously known systems.

In one aspect, the present disclosure provides an NMR apparatus having an AC voltage generator, a transmit switching circuit, a coil switching network, an array of two or more detection coils, a set of receive switching circuits with one switching circuit for each detection coil, and a set of preamplifier circuits with input impedance substantially greater that the impedance of each respective detection coil at the intended operating frequency. In one embodiment, the AC generator produces an alternating current waveform that is routed through one or more detection coils during transmit mode. The transmit switching circuit includes a pair of passive or active switching devices or relays. The transmit switches are closed during transmit to enable current to flow between the transmitter and the transmit coil or coils. The transmit switches are open during receive mode to isolate the transmitter from the coils and prevent noise from the transmitter from degrading the quality of received signals. The coil switch may be a set of passive or active switches or connectors, that enables an operator to select a specific coil or coils on which to transmit, and to select specific polarizations or current directions for each transmit coil. A passive coil switch may comprise manual contactors, manual switches, or electrical connectors with repositionable jumper cables. An active coil switch may comprise one or more sets of electromechanically or electronically controlled switches.

In one embodiment, the detection coil array includes two or more detection coils with individually accessible terminals. The receive switching circuit includes actively controlled-electromechanical or solid state relays, with one pair of relays for each receive channel. The receive relays are open during transmit to isolate the receive electronics from high voltages and currents on the transmit coil or coils, which may damage the receive electronics. The receive relays are closed during receive mode to enable the receive electronics to sense the NMR signal voltage induced on the detection coils. The preamplifier circuit, in an embodiment, includes signal conditioning and amplification elements. The preamplifier circuit has a characteristic input impedance, $Z_{in}$, that is substantially greater than the impedance of each respective detection coil at the intended operating frequency.

Prior to explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION

Figure 1:
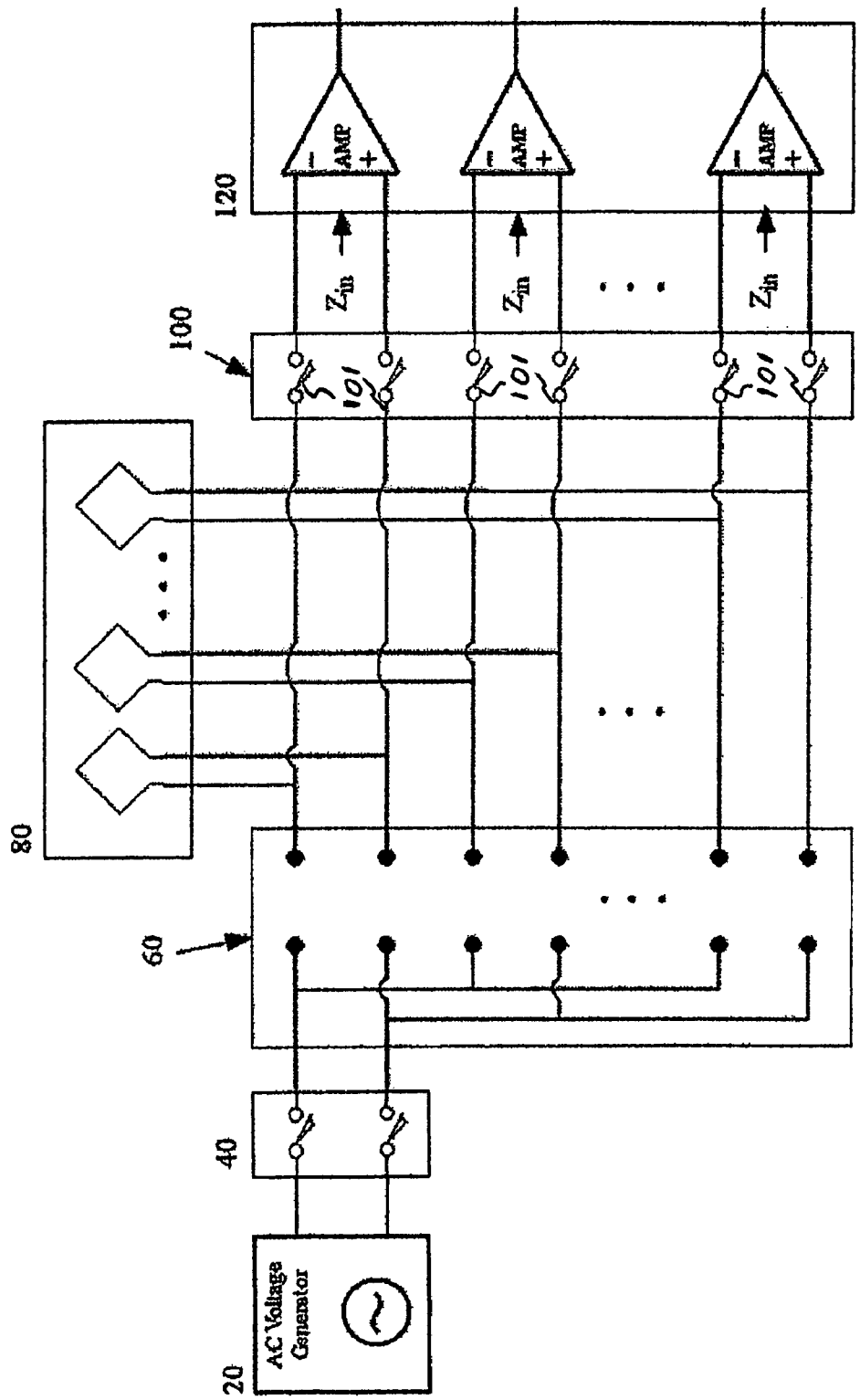
FIG. 1 is a diagram of components of an NMR apparatus of an embodiment of the present disclosure.

The present disclosure recognizes that previously known NMR devices may be suitable for the particular purpose to which they address, but they are not as suitable for allowing multicoil NMR detection and imaging to be performed efficiently at low operating frequencies. The present disclosure recognizes that a significant problem with conventional NMR systems is that existing devices designed for low-field NMR detection are not practical for multi-channel applications due to mutual coupling between adjacent coils during receive mode. For example, existing low-field NMR devices often employ a tuning capacitor in parallel with the detection coil to maximize the NMR signal voltage at the input to a preamplifier circuit. The use of a parallel tuning capacitor creates a relatively low-impedance circuit, and allows currents to flow freely through the detection coils. This is generally not a problem when performing NMR detection with a single detection coil. However, if multiple detection coils are to be employed, the free flow of currents through the detection coils may cause mutual coupling between adjacent coils resulting in partial mixing of signals among the coils, which in turn can complicate imaging efforts.

The present disclosure also recognizes that another problem with conventional NMR apparatus are existing devices designed for low-field NMR detection do not provide for switching between various transmit coils in an array, nor do they provide a mechanism for transmitting on more than one transmit coil at the same time, nor do they provide a mechanism for transmitting on more than one set of polarities for a set of respective transmit coils. Also, another problem is that existing multi-channel NMR detection devices are not practical for implementation in low-field NMR, where the Larmor frequency can be measured in the range of kHz, rather than MHz, and where electrical wavelengths can be comparatively long. For example, practical circuits for high-field multiple coil NMR, including medical MRI, utilize one or more transmission line segments equal in length to an integer multiple of a quarter wavelength, to both isolate transmitter noise and minimize mutual coupling between coils in the receive mode. These existing designs are not practical for implementation in low-field NMR, where the Larmor frequency can be measured in the range of kHz, rather than MHz, and where electrical wavelengths can be comparatively long. In Earth's field NMR applications, the resonant frequency is approximately 2 kHz, and a quarter-wavelength transmission line segment at this frequency could be as long as 37.5 kilometers.

The present disclosure provides a multicoil NMR detection and imaging apparatus that provides reduced mutual coupling between coils in low-field multichannel NMR applications. The present disclosure also provides a multicoil NMR detection and imaging apparatus that isolates noise caused by the transmitter during the receive mode, without requiring the use of long transmission line segments as in existing systems. The present disclosure further provides a multicoil NMR detection and imaging apparatus that provides high signal gain and low preamplifier input noise during receive mode. Also provided is a multicoil NMR detection and imaging apparatus that provides effective isolation of the receiver electronics during transmit mode, when high voltages and currents may be present on the detection coils. The present disclosure even further provides a multicoil NMR detection and imaging apparatus that enables transmission on either a single selected coil, or on multiple selected coils simultaneously, and enables transmission on multiple coils in parallel or series with each other, and enables various combinations of individual coil polarities when transmitting on multiple coils at the same time. Various other features and advantages of the present disclosure will be readily apparent to one of skill in the art, and it is intended that these features and advantages are within the scope of the present disclosure.

The present disclosure, in various embodiments, provides an apparatus for efficient multi-coil NMR detection and imaging at low static field strengths and low operating frequencies. In one embodiment, high input impedance preamplifier circuits are provided for the express purpose of suppressing current flow, and hence suppressing mutual coupling among the plurality of detection coils during receive mode. Existing low-field NMR detection and imaging devices also provide no means of selectively routing the NMR excitation pulse(s) through individual detection coils, or through various series of parallel combinations of detection coils. The present disclosure, in an embodiment, provides a flexible coil selection switching mechanism which enables the user to route the NMR excitation pulses through one or more coils in the array, in various series and/or parallel combinations, and with various selected polarities or current directions for each coil.

The present disclosure recognizes that none of the previously disclosed mechanisms as described above are practical for multi-coil NMR detection at low operating frequencies. Transmission line segments of lengths on the order of one quarter wavelength are excessively long to be practical at low operating frequencies. At low operating frequencies, a pair of parallel crossed diodes across the transmitting coil terminals will have the effect of short circuiting the transmit current in transmit mode, preventing efficient activation of the NMR processes. At low operating frequencies, the detection coils will have a correspondingly low self-impedance, and hence it is not practical to realize pre-amplifier circuits with substantially lower input impedance than the detection coils.

The present disclosure overcomes the limitations of existing multi-coil NMR detection devices for low field NMR detection, by providing preamplifier circuits with a high input impedance relative to the detection coils at the intended low operating frequency. Embodiments described herein also obviate the requirements for quarter-wavelength transmission line segments and parallel-crossed diodes by providing actively-controlled electromechanical relays or solid state relays at the receive side of the detection coils.

Figure 2:
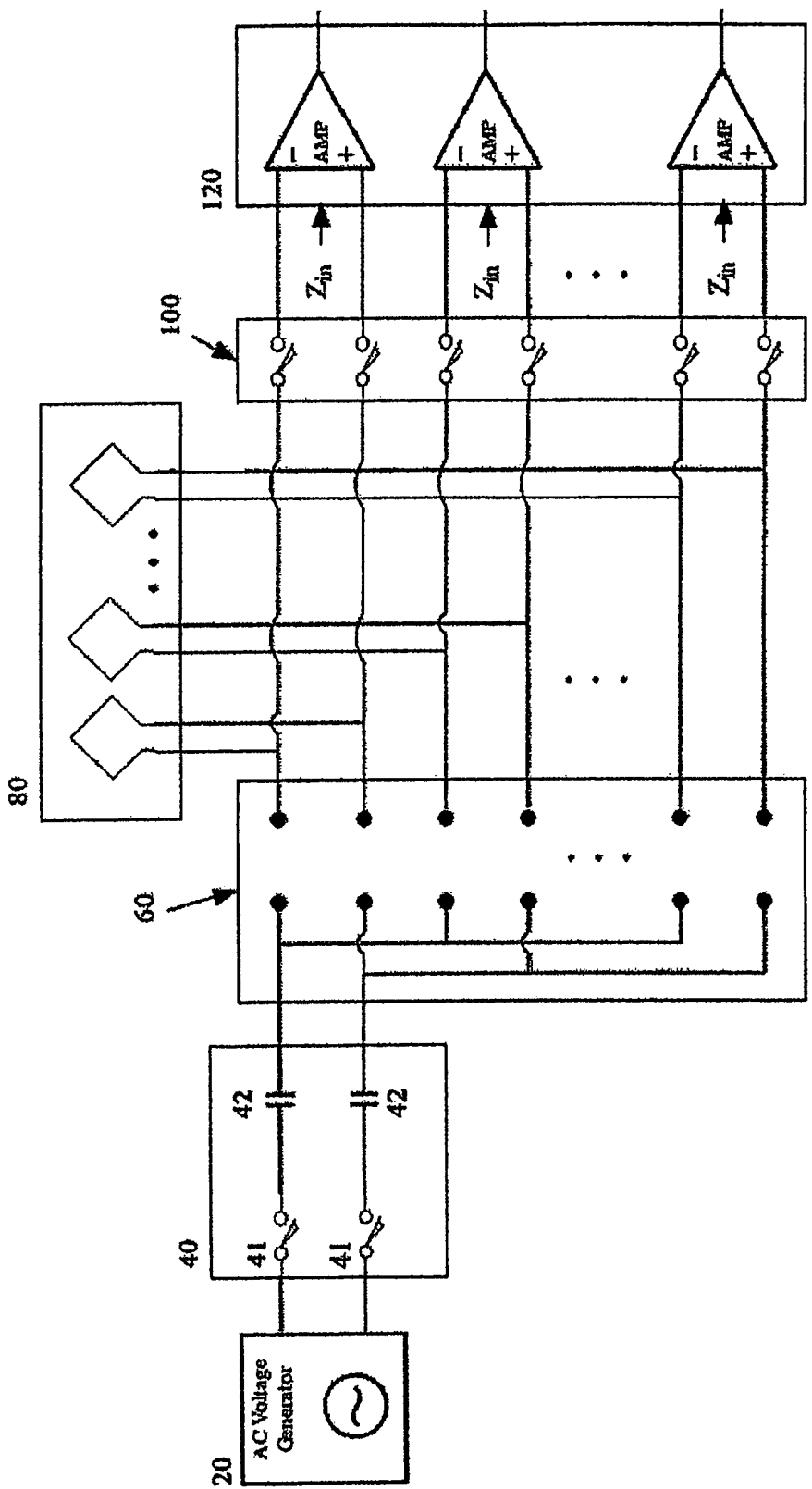
FIG. 2 is a diagram of an embodiment of an NMR apparatus having series tuning capacitors on the coil side of the transmit switch.
Figure 3:
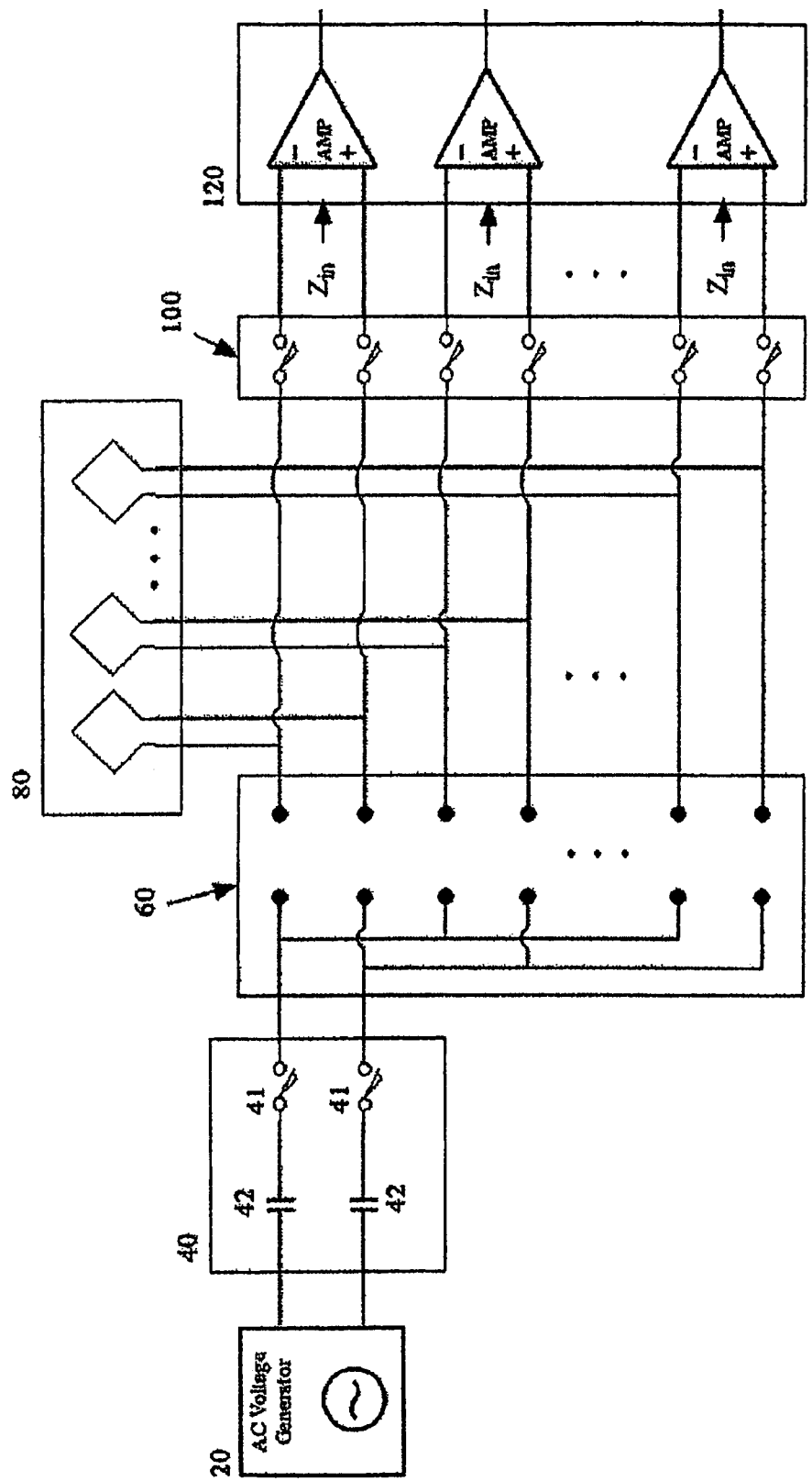
FIG. 3 is a diagram of an embodiment of an NMR apparatus having series tuning capacitors on the transmitter side of the transmit switch.
Figure 4:
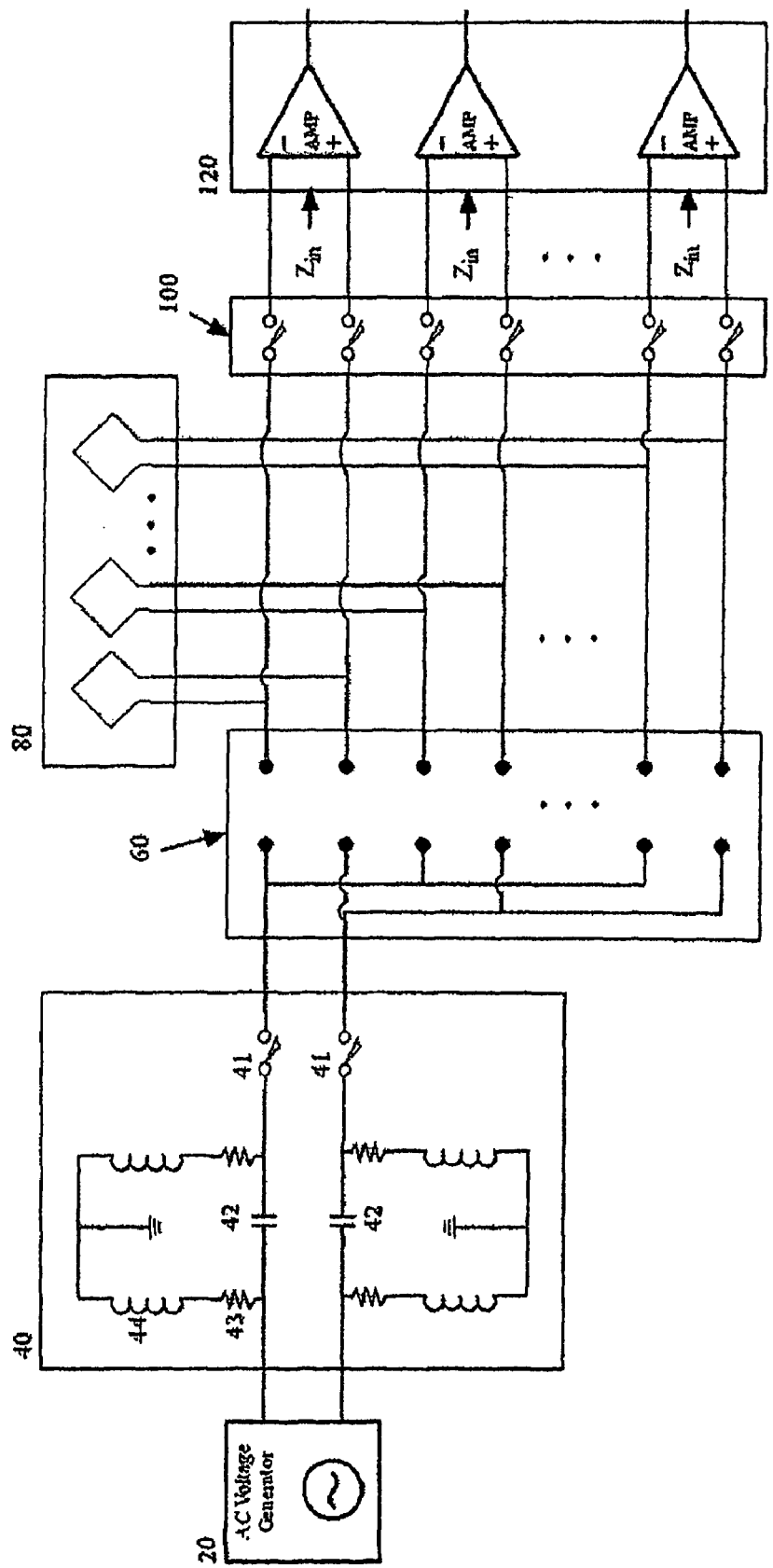
FIG. 4 is a diagram of an embodiment of an NMR apparatus having voltage bleeder elements on both sides of the tuning capacitors.

Turning now descriptively to the drawings, and with reference to FIGS. 1-11, illustrated are several exemplary embodiments of a multicoil NMR detection and imaging apparatus. With reference first to FIG. 1, the NMR detection and imaging apparatus of this embodiment comprises an AC voltage generator 20, a transmit switching circuit 40, a coil switch 60, an array of two or more detection coils 80, a set of receive switching circuits 100 with one switching circuit for each detection coil 80, and a set of preamplifier circuits 120 with input impedance substantially greater that the impedance of each respective detection coil 80 at the intended operating frequency. In operation, the AC generator 20 produces an alternating current waveform that is routed through one of more detection coils 80 during transmit mode. The transmit switching circuit 40 includes switching devices that are opened or closed to provide an electrical connection between the AC voltage generator 20 and the detection coils 80. The switching devices of the transmit switching circuit may include a pair of passive or active switching devices or relays 41, as illustrated in the embodiment of FIG. 2. The transmit switches 41, in this embodiment, are closed during transmit to enable current to flow between the transmitter, namely AC voltage generator 20, and the transmit coil or coils 80. The transmit relays 41 are open during receive mode to prevent noise from the transmitter from degrading the quality of received signals. The coil switch 60 is a set of passive or active switches or connectors, that enables the selection a specific coil or coils on which to transmit during transmit mode, and to select specific polarizations or current directions for each transmit coil. A passive coil switch may comprise manual contactors, manual switches, or electrical connectors with re-positionable jumper cables. An active coil switch may comprise one or more sets of electromechanically or electronically controlled switches.

The detection coil array 80 includes two or more detection coils with individually accessible terminals. The receive switching circuit 100 of this embodiment includes switching devices that are opened or closed to provide an electrical connection between the detection coils 80 and the set of preamplifier circuits 120. In the embodiment of FIG. 1, the switching devices are actively controlled-electromechanical or solid state relays 101, with one pair of relays for each receive channel. The receive relays 101 are open during transmit to prevent high voltages and currents on the transmit coil or coils 80 from damaging the receive electronics. The receive relays 101 are closed during receive mode to enable the receive electronics to sense the NMR signal voltage induced on the detection coils 80. The preamplifier circuit 120, in an embodiment, includes signal conditioning and amplification elements. The preamplifier circuit 120 has a characteristic input impedance, $Z_{in}$, that is substantially greater than the impedance of each respective coil 80 at the intended operating frequency of the NMR detection and imaging apparatus.

The AC generator 20 produces an alternating voltage and current waveform which is routed through one or more coils 80 in transmit mode to activate the NMR spin process in the static magnetic field B0. The static magnetic field may be the Earth's magnetic field, or any other static magnetic field in which the NMR sample is located. The AC generator 20 typically includes an AC signal generation device and a power amplifier. The AC signal generation device generates a low-voltage version of the NMR excitation waveform. The power amplifier transforms this low-voltage waveform into a current waveform which is routed through the selected transmit coil or coils 80. The signal generator typically comprises a computer-controlled digital output device, or computer-controlled digital to analog converter. The power amplifier may be any device suitable for generating the current waveforms required for a particular application.

The purpose of the transmit switch 40 is to enable current to flow freely from the transmitter to the coil or coils during transmit mode, and to isolate transmitter noise from the coils and receive electronics during receive mode. The transmit switch 40 includes a pair of passive or active switches 41, illustrated for example in FIG. 2, wired in series between the AC generator and the selected coils or coil switching circuit. The transmit switches 41 are closed during transmit to enable current to flow between the AC generator and the transmit coil or coils. The transmit relays are open during receive mode to prevent noise from the AC generator from degrading the quality of received signals. The transmit switch may comprise a pair of electromechanical or solid state relays, which are opened and closed via electronic means. In one embodiment, the transmit relays are computer-controlled electromechanical relays which produce a physical electrical contact when closed, and an electrical open circuit when open. This open circuit provides a highly effective electrical isolation between the transmitter and receive electronics during receive mode. The transmit switch may also comprise passive devices, such as series crossed diodes, which conduct current when high voltage is applied by the transmitter and which effectively isolates noise from the transmitter when high voltage is not applied by the transmitter. The transmit switch, in one embodiment, includes series capacitors 42 for tuning the transmit coil, as illustrated in the exemplary embodiments of FIGS. 2 and 3. The series tuning capacitors 42 may be located on either the generator side or the coil side of the switching elements. The transmit switch may optionally include resistors 43 and or inductors 44 to bleed the DC charge of the optional tuning capacitors 42, as illustrated in the exemplary embodiment of FIG. 4.

Figure 6:
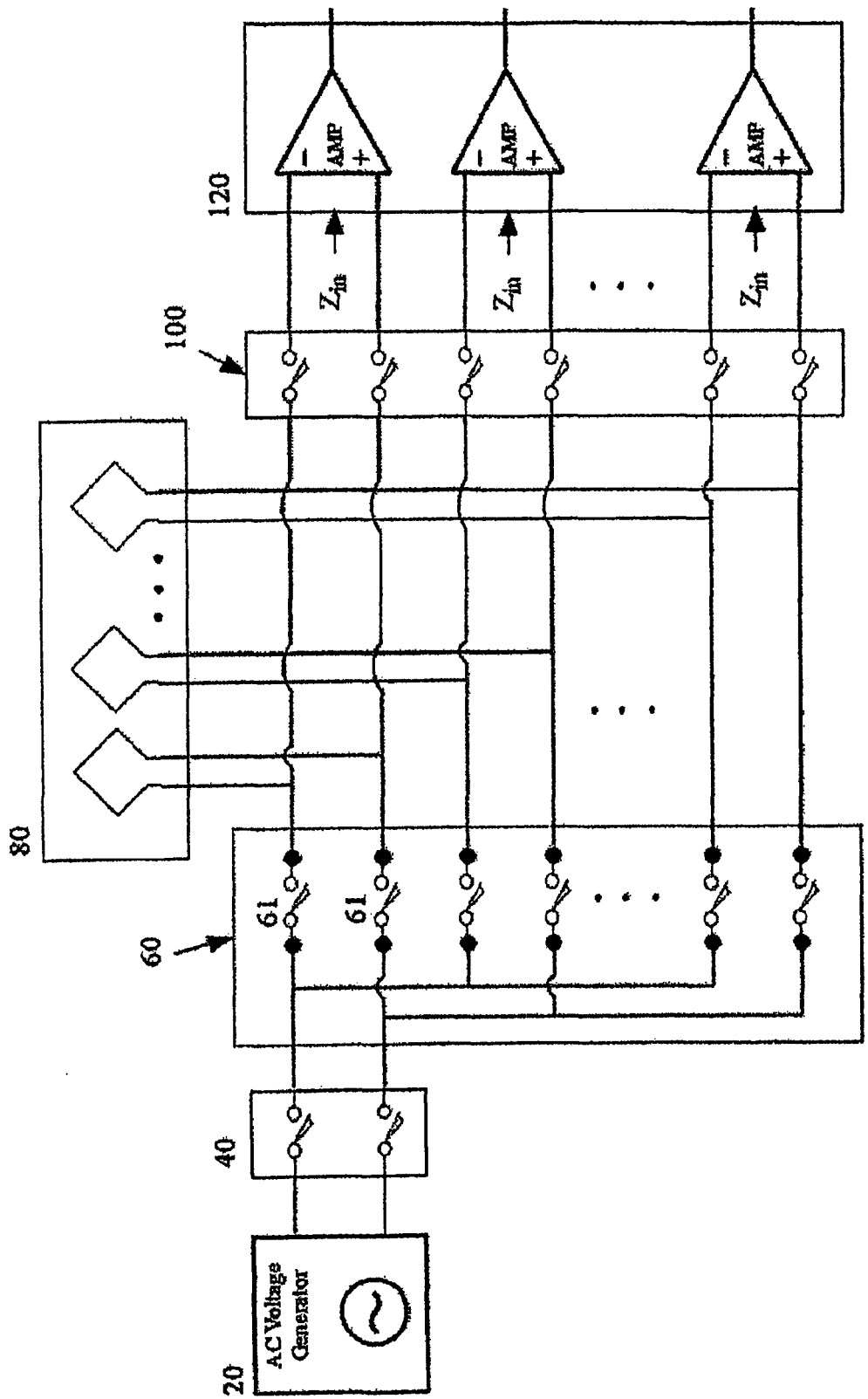
FIG. 6 is a diagram of an embodiment of an NMR apparatus having individually-addressable coil switches.
Figure 7:
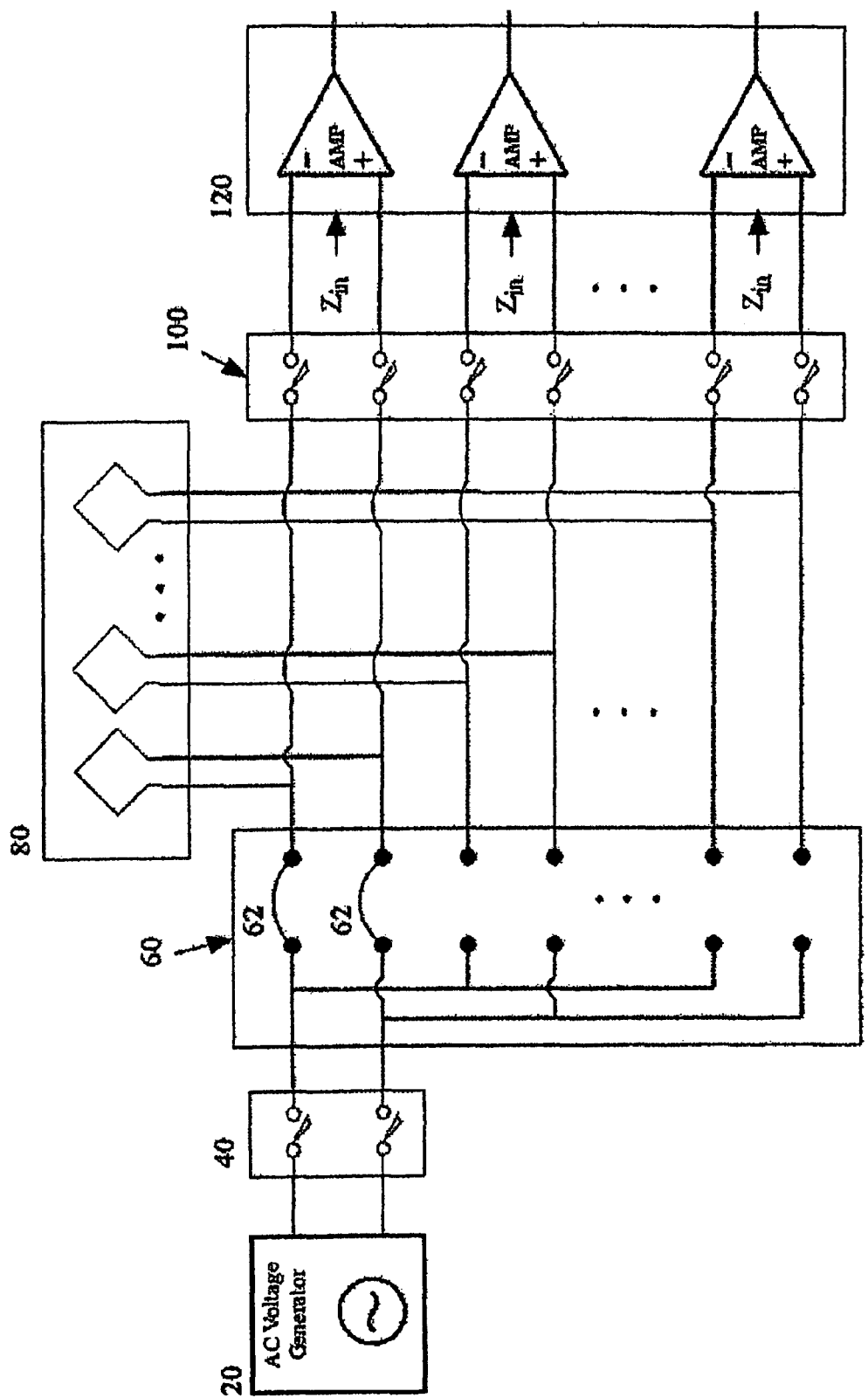
FIG. 7 is a diagram of an embodiment of an NMR apparatus having manual jumpers used to select a single transmit coil.
Figure 8:
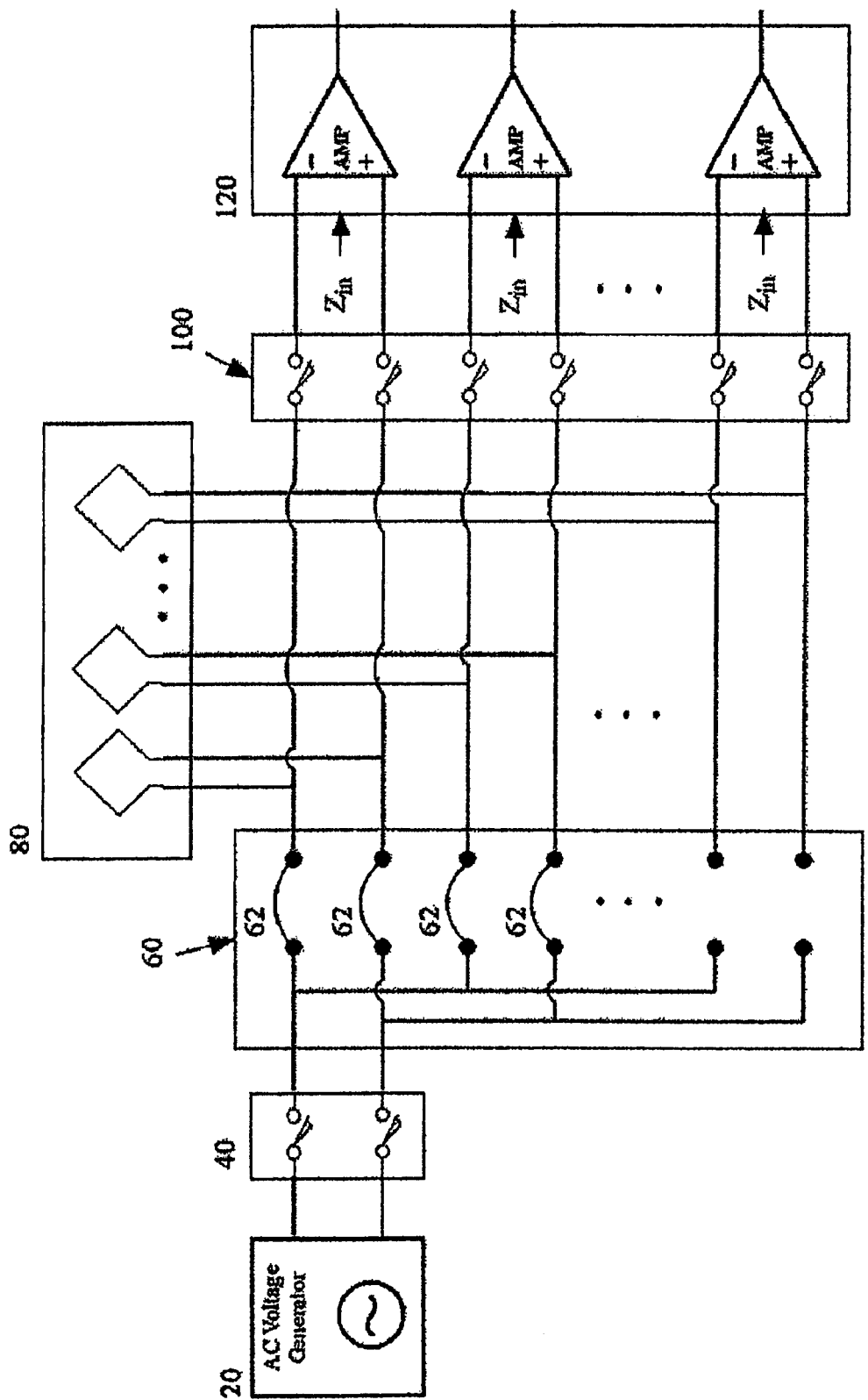
FIG. 8 is a diagram of an embodiment of an NMR apparatus having manual jumpers used to select two transmit coils in parallel.

The coil switch 60 is a set of passive or active switches or connectors, that enable the selection a specific coil or coils on which to transmit, and to select specific polarizations or current directions for each transmit coil. A passive coil switch may comprise manual contactors, manual switches, or electrical connectors with repositionable jumper cables. An active coil switch may comprise one or more sets of electromechanically or electronically controlled switches. The switching devices or connectors within the switching network are not required to open or close during the course of an NMR signal acquisition sequence. In an exemplary embodiment, the coil switching network 60 comprises a pair of terminals at the output of the transmit switch, a pair of open contacts for each coil, and jumper cables 62 or bus bars 62 which are connected manually to route the transmitter voltage and current through a selected coil or coils, such as illustrated in the exemplary embodiments of FIGS. 7-10. In another embodiment, the electrical connections between the transmit switch and specific transmit coils may be made by active devices 61, such as relays or contactors, as illustrated in FIG. 6.

The detection coil array 80 is an array of two or more conducting loops (coils) used for detection of NMR signals. Each detection coil has a pair of individually addressable terminals for sensing the differential voltage across the coil. In various embodiments, all coils in the array may be used for both transmission of the excitation current waveform and detection of the resulting NMR signals. The receive switching circuit may include actively controlled-electromechanical or solid state relays, with one pair of relays for each receive channel. The receive switch 100 includes of one pair of actively-controlled receive switching elements 101 for each detection coil in the array. The receive switching elements are open during transmit mode to prevent the high voltages and currents on the transmit coil or coils from damaging the receive electronics. The receive switching elements are closed during receive mode to enable amplification and detection of the NMR-induced voltage signal on each detection coil. In a preferred embodiment the receive switching elements 101 are actively controlled electromechanical or solid-state relays. In one embodiment, illustrated in FIG. 5, transient voltage suppression (TVS) circuits or devices 102 are employed on the receiver side of the receive switching elements 101. The purpose of the TVS circuits 102 is to suppress transient voltages that could otherwise damage the preamplifier circuitry 120. The TVS devices may comprise any combination of crowbar circuits, gas discharge tubes, varistors, parallel crossed diodes or Zener diodes.

Figure 5:
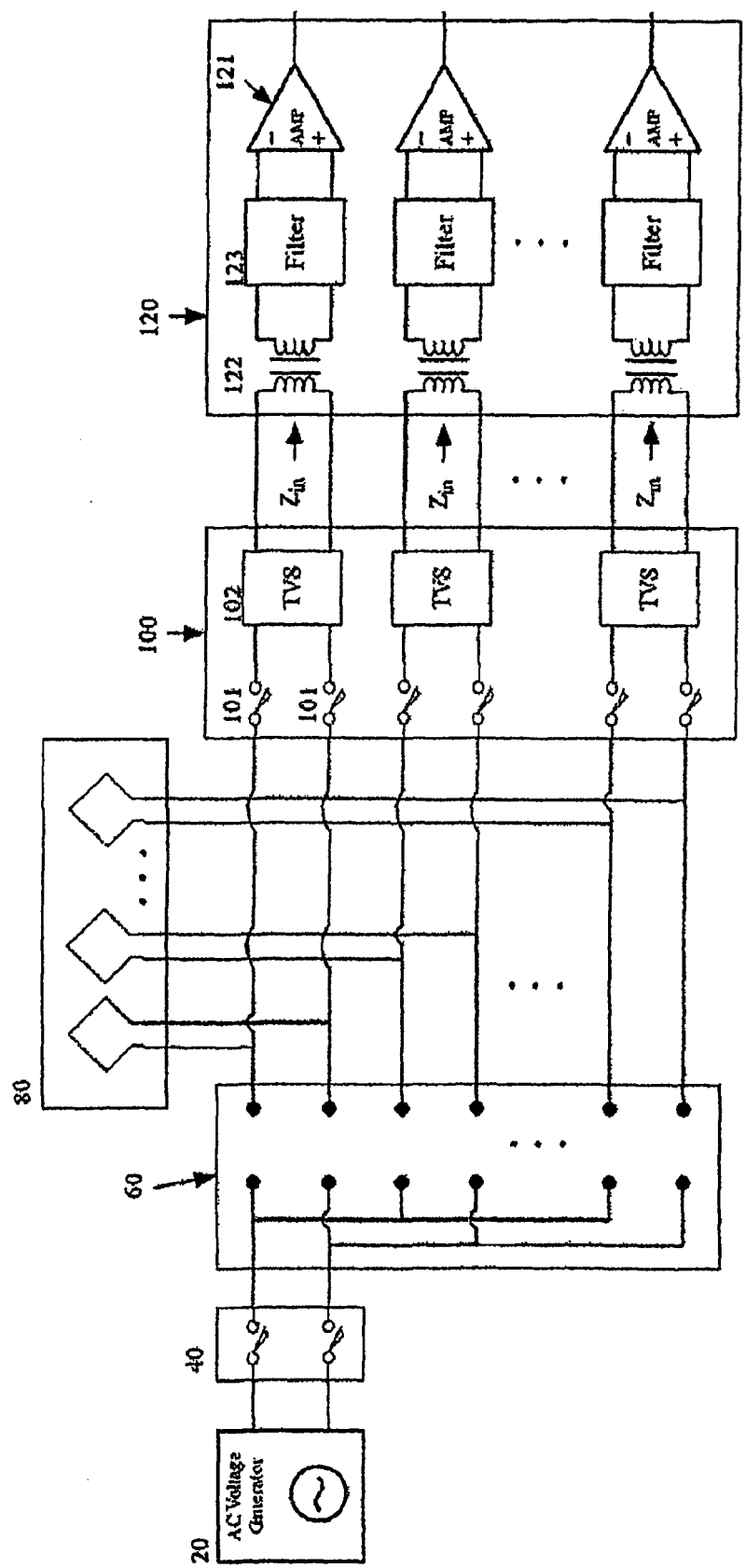
FIG. 5 is a diagram of an embodiment of an NMR apparatus having optional subcomponents of the preamplifier circuit.

The preamplifier circuit 120 provides isolated signal conditioning and preamplification of the differential NMR voltage signal on each detection coil. The input impedance to each preamplifier channel, $Z_{in}$, is substantially greater than the impedance of each respective detection coil at the intended operating frequency. The high input impedance of the preamplifier circuit suppresses the flow of currents through the detection coils, and hence suppresses mutual coupling between coils, during receive mode. The preamplifier circuit comprises a pre-amplifier 121 and may include any optional combination of transformers 122 and filters 123 which combine to present a high input impedance to each coil during receive mode, such as illustrated in the embodiment of FIG. 5. One exemplary embodiment uses a high input impedance differential pre-amplifier on each receive channel. Another exemplary embodiment uses a step-up voltage transformer 122 as the input stage. The step-up voltage transformer, combined with other circuitry in the preamplifier circuits, provides an input impedance substantially higher than the impedance of each respective detection coil at the intended operating frequency.

Figure 9:
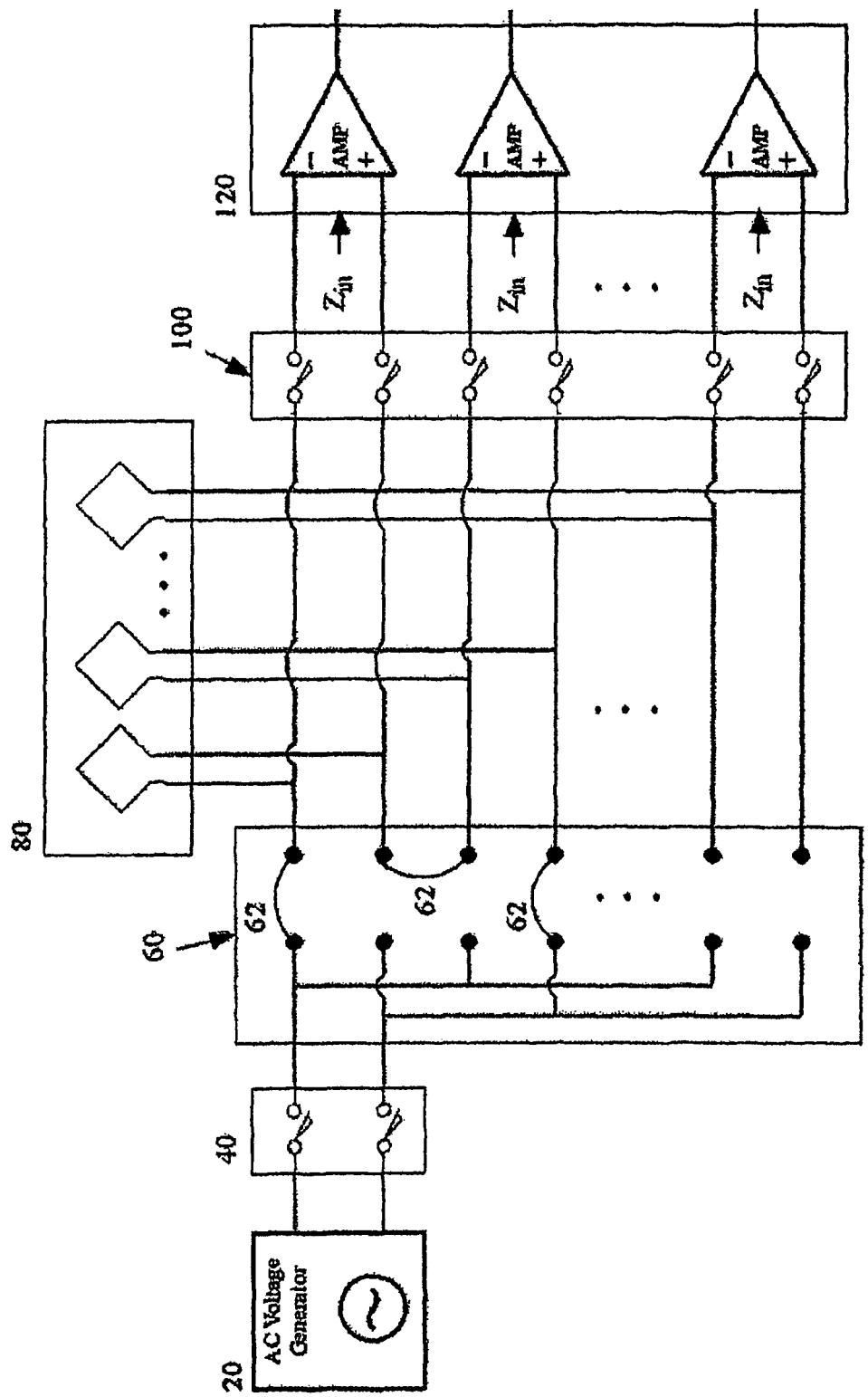
FIG. 9 is a diagram of an embodiment of an NMR apparatus having manual jumpers used to select two transmit coils in series.
Figure 10:
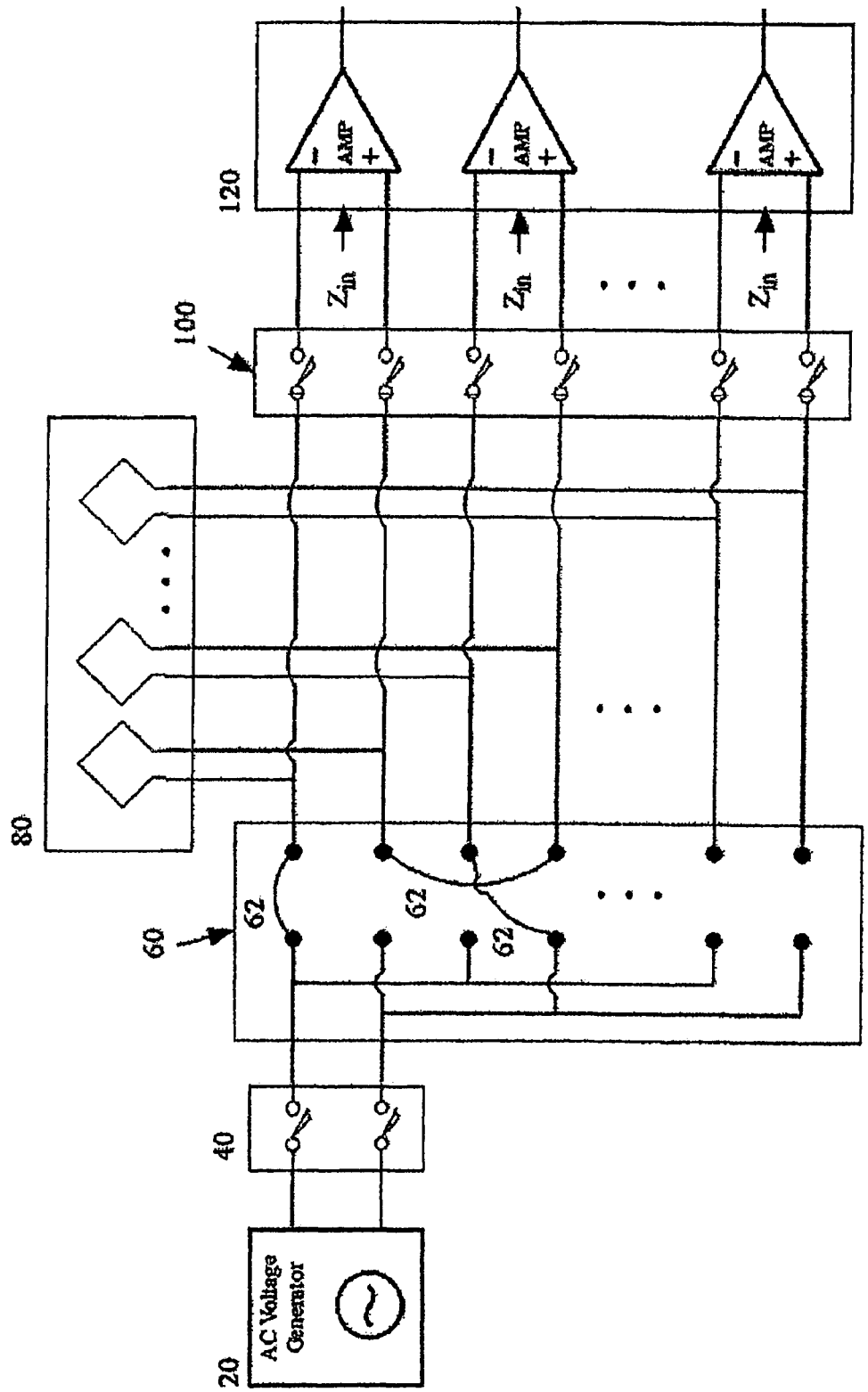
FIG. 10 is a diagram of an embodiment of an NMR apparatus having manual jumpers used to select two transmit coils in opposite series.
Figure 11:
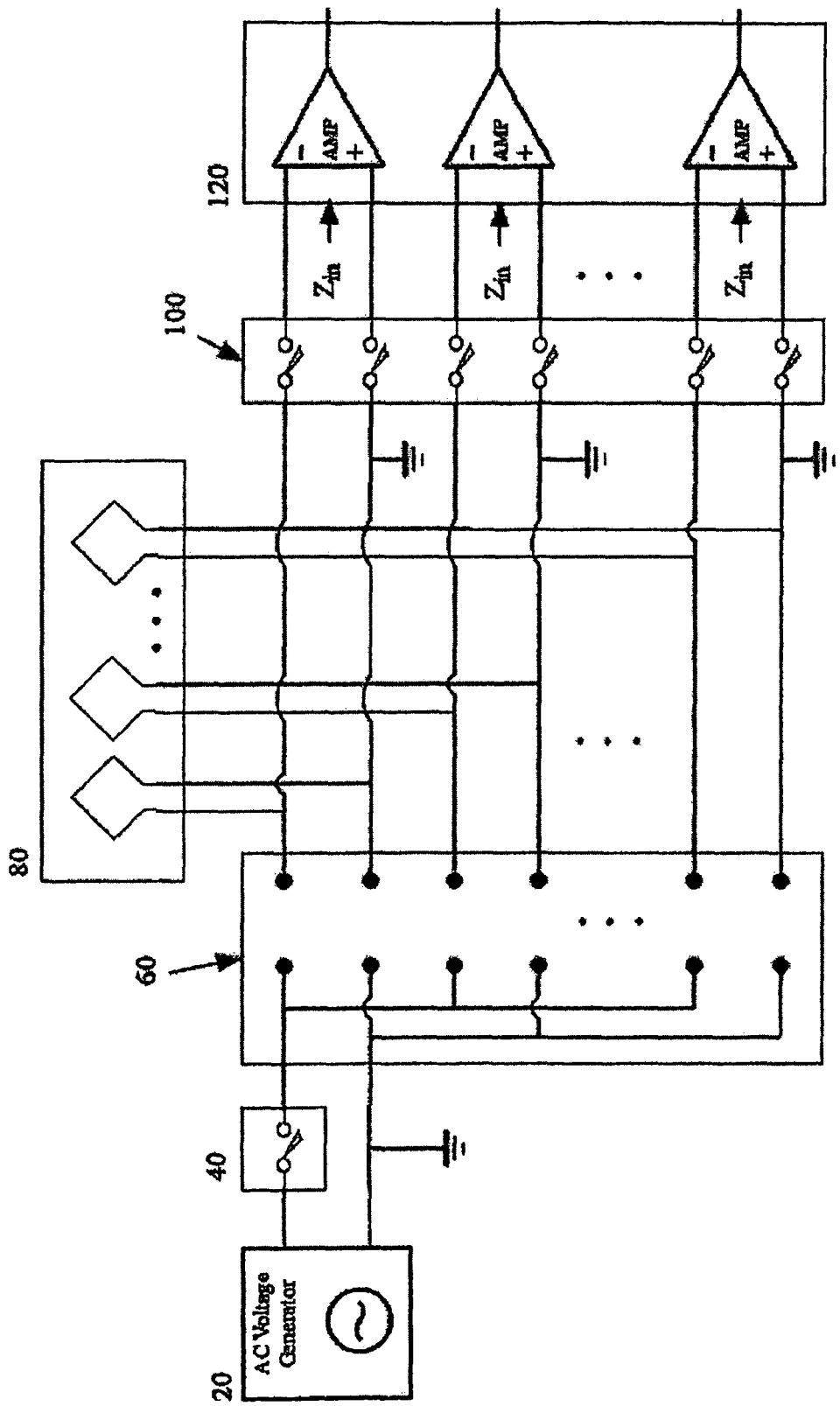
FIG. 11 is a diagram of an embodiment of an NMR apparatus having a common ground connected to one side of an AC voltage generator and one terminal of each detection coil.

The AC generator 20 is connected to the transmit switch 40 by a pair of parallel electrical lines with appropriate connectors. The transmit switching elements 41 are connected in series with the optional tuning capacitors 42. The series tuning capacitors 42 may be located on either the AC generator side or the coil side of the transmit switching elements 41. The optional bleeder resistors 43 and/or bleeder inductors 44 may be connected from one or both sides of each tuning capacitor to a common ground. The transmit switch 40 is connected to the coil switch 60 by a pair of parallel electrical lines with appropriate connectors. The coil switching contactors 61 are connected between the input and output terminals of the coil switch. The coil jumper cables 62 or bus bars 62 are connected between the coil switch input terminals and one or more coil terminals using appropriate connectors. The coil jumper cables may also be used to connect the terminals of one or more coils in series, such as illustrated in FIG. 9. Each coil in the detection coil array 80 connects to the receive switch 100 by a pair of electrical lines with appropriate connectors. Within the receive switch, the receive switching elements 101 may be connected in series with the optional TVS circuits or devices 102. The receive switch 100 connects to the preamplifier circuit 120 via a set of parallel electrical lines with appropriate connectors, with one pair of electrical lines for each detection coil. Within the preamplifier circuit 120, the preamplifier 121 may be wired in series with the optional transformer 122 and the optional filter 123. In an exemplary embodiment, the optional transformer 122 precedes the optional filter 123, which precedes the preamplifier 121.

The apparatus may be used to perform a multi-channel NMR detection method in any arbitrary static magnetic field BO. The apparatus is intended for enhanced detection of NMR signals in relatively low static magnetic fields, where quarter-length transmission line segments are an impractical means for isolating the AC generator from the receive electronics. The transmit switching elements 41 may be either electromechanical relays, solid-state relays, or series-crossed diodes. The coil switching elements 61 and 62 may be either electromechanical relays, manual contactors, or any form of manually adjustable jumper cable or bus bar. The detection coils may be single-turn or multiple-turn conducting loops. The optional transient voltage suppression devices 102 may include any combination of parallel-crossed diodes, Zener diodes, crowbar circuits, varistors, spark gaps, or gas discharge tubes. The optional transformer 122 may have an arbitrary turns ratio and voltage gain, provided that the combined effective input impedance of each preamplifier channel is substantially greater than the impedance of each respective detection coil at the intended operating frequency. The optional filter 123 may effect a high-pass, bandpass, or low-pass response. In an example multi-channel NMR detection method, the AC generator 20 generates an alternating voltage waveform, which drives current through the selected coils during transmit mode. During transmit mode, the transmit switch 40 is closed, allowing current from the AC generator 20 to flow through the coil switch 60 to the selected coil or coils in the detection coil array 80. During transmit mode one or more detection coils are connected in series or in parallel with the output of the transmit switch, using contactors 61 or jumper elements 62, to make the desired connections. The resulting alternating current through one or more detection coils creates an alternating magnetic field B1 which tips the NMR spin magnetization away from the static field axis BO, and sets the spin magnetization precessing about the BO field at the Larmor frequency. The receive switching elements 101 are open during transmit mode to prevent the high voltage and currents on one or more detection coils from damaging the receive electronics. The optional transient voltage suppression devices 102, in an embodiment, act as a failsafe mechanism to limit the voltage applied to the input of the preamplifier circuit in case the receive switching elements 101 fail to open. The optional series tuning capacitors 42 may be used to balance the inductive portion of the transmit coil impedance during transmit mode, and hence increase the current flow through the transmit coil or coils during transmit mode. The optional bleeder resistors 43 and/or bleeder inductors 44 may be used to prevent DC voltages from accumulating on the tuning capacitors 42. In one embodiment, after the transmit pulse is applied, the transmit switching elements 41 are opened as quickly as possible to inhibit residual current flow in the coils and isolate noise from transmitter during receive mode. After the transmit pulse is applied the receive switching elements 101 are switched to the closed state as quickly as possible to enable detection of the NMR-induced voltages on the detection coils. As discussed above, the preamplifier circuit 120 is designed such that the input impedance of each receive channel, $Zi_n$, is substantially greater than the impedance of each channel's respective detection coil at the intended operating frequency. The high input impedance of the preamplifier circuit 120 has the effect of inhibiting current flow through the coils during receive mode, and hence inhibiting mutual coupling between detection coils in receive mode. The optional transformer 122 acts as a low-noise differential preamplifier stage. The optional filter 123 is used to limit spectral content outside the frequency bands of interest, and hence reduce the dynamic range of the detected signal.

The attached figures also illustrate various optional sub-components of preferred embodiments of the invention, including series capacitors 42 for tuning the transmit coil or coils during transmit mode, active electromechanical or solid-state transmit switches 41, a generic switching network contactors 61 or jumpers 62 for routing the transmit current through one or more selected coils, electromechanical receive switches 101, transient voltage suppression devices 102, optional analog filter circuits 123, optional transformers 122, and high-input impedance pre-amplifiers 121.

As will be understood, the above exemplary embodiments are provided for purposes of discussion and illustration, and one of skill in the art will readily recognize numerous variants that may be implements based on a specific application. For example, another embodiment uses a parallel tuning capacitor on either side of the transmit switching circuit, instead of the series tuning capacitors depicted in FIGS. 2 and 3. In another embodiment, illustrated in FIG. 11, one side of the AC voltage generator and one terminal of each detection coil are connected to a common ground. In yet another embodiment, the control signals used to open and close the transmit and receive switches are timed so as to cause the transmit switches to open immediately after the end of the NMR excitation pulse, and to cause the receive switches to close immediately after the end of the NMR excitation pulse. If necessary, the control signals for opening the transmit switches and closing the receive switches may be initiated prior to the end of the NMR excitation pulse, to allow for device-specific opening and closing delays. In still another embodiment, the transmit switches comprise electromechanical relays, and a transient voltage suppression circuit is wired in parallel with the relay drive coils to allow a controlled level of back electromotive force to be generated while the relay is opening. This embodiment enables the circuit designer to minimize the opening time for the transmit relays while simultaneously allowing a maximum transient voltage across the relay coil terminals. One other embodiment provides an active or passive de-Qing circuit to reduce transient voltages on the detection coils immediately following the NMR excitation pulse(s). Such a de-Qing, or Q-damping circuit, is employed to lower the Q-value of each detection coil immediately after the transmit pulse. The Q-damping circuit thus works to decrease the time required to bleed transient voltages from the coil and reduces recovery time of the preamplifier circuit The NMR detection and imaging apparatus of various embodiments may be interconnected to external systems that provide control and data collection functionality. Control systems may provide control to the AC voltage generator, various switches, in order to provide the desired configuration for the application/collection of signals to/from the detection coils 80. Data collection systems may include systems that receive the output of the preamplifier circuits and process the outputs to generate an NMR image. Such data collection systems and imaging techniques will be readily understood by one of skill in the art. Furthermore a single control system may provide both control and data collection/imaging functionality.

As to a further discussion of the manner of usage and operation of the present invention, the same should be apparent to one of skill in the art from the above description. Accordingly, no further discussion relating to the manner of usage and operation will be provided. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A Nuclear Magnetic Resonance (NMR) apparatus configured for low-field NMR measurements, comprising:
   a transmitter configured to produce an Alternating Current (AC) voltage and current waveform with an operating frequency, wherein the waveform is routed through one or more coils in transmit mode to activate NMR spin in a sample located within the low-field; and
   two or more detection coils connected to separate receive switching circuits, each receive switching circuit comprising:
      one or more receive switches configured to isolate receive electronics from high voltage during transmit mode, and to enable receive electronics detection of signals in a detection coil during receive mode; and
      a preamplifier circuit having input impedance greater than the impedance of a detection coil at the operating frequency.

2. The NMR apparatus of claim 1, wherein the transmitter comprises an AC voltage generator, the AC voltage generator comprising an AC signal generation device and a power amplifier, wherein the AC signal generation device generates a low-voltage version of an NMR excitation waveform, wherein the power amplifier transforms the low-voltage waveform into a current waveform, and wherein the current waveform is routed through one of more coils during transmit mode.

3. The NMR apparatus of claim 2, wherein the current waveform is routed through a coil switching network to one or more selected coil(s).

4. The NMR apparatus of claim 2, wherein the AC signal generation device comprises a computer-controlled digital output device.

5. The NMR apparatus of claim 1, further comprising a coil switching network electrically connected to the transmitter and two or more coils, the coil switching network configured to selectively connect one or more of the coils to the transmitter during transmit mode.

6. The NMR apparatus of claim 5, wherein the coil switching network comprises at least two switches that enable an electrical connection to one or more selected coils.

7. The NMR apparatus of claim 6, wherein the coil switching network comprises at least two switches that enable the selection of specific polarizations or current directions for each coil.

8. The NMR apparatus of claim 6, wherein the coil switching network comprises two or more passive coil switches.

9. The NMR apparatus of claim 6, wherein the coil switching network comprises two or more active coil switches.

10. The NMR apparatus of claim 1, wherein the detection coils comprise individually accessible terminals.

11. The NMR apparatus of claim 1, wherein the receive switching circuits comprise actively controlled receive relays, with one pair of relays for each detection coil.

12. The NMR apparatus of claim 11, wherein the receive relays are open during the transmit mode to isolate high voltages and currents on the one or more coils in transmit mode from the preamplifier circuits.

13. The NMR apparatus of claim 11, wherein the receive relays are closed during the receive mode to enable the preamplifier circuits to sense NMR signal voltage on the detection coils.

14. The NMR apparatus of claim 1, wherein one or more of the preamplifier circuits comprise signal conditioning and amplification elements.

15. The NMR apparatus of claim 1 wherein one or more of the preamplifier circuits include a step-up voltage transformer that, combined with other circuitry in a preamplifier circuit, provides an input impedance configured to inhibit current flow through the detection coils in the receive mode.

16. The NMR apparatus of claim 1, further comprising a Q-damping circuit configured to lower the Q-value of each detection coil immediately after a transmit pulse.

17. The NMR apparatus of claim 1, further comprising a transmit switching circuit electrically connected to the transmitter, the transmit switching circuit configured to enable current flow between the transmitter and the coils in transmit mode, and to isolate the transmitter from the detection coils in receive mode.

18. The NMR apparatus of claim 17, wherein the transmit switching circuit includes one or more electrical switches selected from the group comprising: crossed diodes, electromechanical relays, semiconducting switches, and transistors.

19. The NMR apparatus of claim 1, further comprising one or more tuning capacitors configured to increase current flow in the one or more coils in transmit mode.

20. The NMR apparatus of claim 19, wherein one or more voltage bleeder elements configured to reduce the accumulation of electrical charges on the tuning capacitors.

21. The NMR apparatus of claim 17, wherein the transmit switching circuit comprises a pair of switching devices that are closed during the transmit mode to enable current to flow between an AC voltage generator and a coil switching network, and that are open during the receive mode to isolate the AC voltage generator from the detection coils.

22. The NMR apparatus of claim 21, wherein the coil switching network includes one or more of an active switch, a passive switch, a relay, a manual contactor, and a jumper cable configured to selectively connect the transmitter to the one or more coils.

23. The NMR apparatus of claim 1, wherein one or more of the receive switching circuits includes a pair of switching devices, each switching device connected to a side of a detection coil.

24. The NMR apparatus of claim 1, wherein one or more of the receive switching circuits includes a switching device connected to a side of a detection coil, and wherein another side of the detection coil is connected to a common ground.

25. The NMR apparatus of claim 1, wherein one or more of the detection coils are configured to serve as one or more of the coils in transmit mode.

26. The NMR apparatus of claim 1, wherein a first stage of the preamplifier circuit includes a step-up voltage transformer.

27. A Nuclear Magnetic Resonance (NMR) apparatus configured for low-field NMR measurements, comprising:
   an AC voltage generator that operates at an operating frequency;
   a transmit switching circuit electrically connected to the AC voltage generator;
   a coil switching network electrically connected to the transmit switching circuit;
   at least two detection coils electrically connected to the coil switching network, the coil switching network selectively connecting one or more detection coils to the transmit switching circuit during a transmit mode;
   at least two receive switching circuits, each receive switching circuit corresponding to a detection coil and selectively connecting the corresponding detection coil during a receive mode; and
   at least two preamplifier circuits, each preamplifier circuit corresponding to a receive switching circuit and detection coil, each preamplifier circuit having input impedance-greater that the impedance of each respective detection coil at the operating frequency.

28. A method for use with a Nuclear Magnetic Resonance (NMR) apparatus comprising an AC voltage generator, a transmit switching circuit, a coil switching network, at least two detection coils, at least two receive switching circuits, and at least two preamplifier circuits, the method comprising:
   in a transmit mode, generating an alternating voltage waveform with the AC generator while maintaining the transmit switching circuit in a closed state, allowing current from the AC generator to flow through the coil switching network to one or more selected detection coils, and while maintaining the receive switching circuits in a opened state, isolating the preamplifier circuits from the detection coils;
   the one or more selected detection coils creating an alternating magnetic field B1 which tips the NMR spin magnetization in a sample away from an axis of a static magnetic field B0, and sets the spin magnetization precessing about the B0 field axis;
   after generating the alternating voltage waveform, opening the transmit switching circuit;
   in a receive mode, closing the receive switching circuits, inhibiting current flow through the detection coils and corresponding mutual coupling between detection coils, and detecting NMR induced voltages on the detection coils with electronics comprising the preamplifier circuits.

29. The method of claim 28, further comprising using the coil switching network to select one or more detection coils in the transmit mode.

30. The method of claim 27, further comprising reducing the dynamic range of a detected NMR signal using a filter.

* * * * *

UNITED STATES PATENT AND TRADEMARK OFFICE
CERTIFICATE OF CORRECTION

PATENT NO.      : 7,986,143 B2
APPLICATION NO. : 12/672503
DATED           : July 26, 2011
INVENTOR(S)     : Walsh Page 1 of 1

It is certified that error appears in the above-identified patent and that said Letters Patent is hereby corrected as shown below:

Column 1, line 16 under the section entitled "CROSS REFERENCE TO RELATED APPLICATIONS" and above the section entitled "FIELD", insert the following section:

-- STATEMENT OF GOVERNMENT SUPPORT
This invention was made with Government support under NSF Grant No. 0450164 awarded by the National Science Foundation. The Government has certain rights in this invention. --.

Column 10, claim 2, at line 55, replace "one of more coils" with "one or more coils".

Column 11, claim 20, at line 49, replace "wherein" with "further comprising".

Signed and Sealed this
Fifteenth Day of November, 2011

David J. Kappos
*Director of the United States Patent and Trademark Office*